(12) United States Patent
Marra

(10) Patent No.: US 8,627,732 B2
(45) Date of Patent: Jan. 14, 2014

(54) DEVICE FOR CHARACTERIZING A SIZE DISTRIBUTION OF ELECTRICALLY-CHARGED AIRBORNE PARTICLES IN AN AIR FLOW

(75) Inventor: Johannes Marra, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 449 days.

(21) Appl. No.: 12/746,788

(22) PCT Filed: Dec. 1, 2008

(86) PCT No.: PCT/IB2008/055026
§ 371 (c)(1),
(2), (4) Date: Jul. 22, 2010

(87) PCT Pub. No.: WO2009/074910
PCT Pub. Date: Jun. 18, 2009

(65) Prior Publication Data
US 2010/0282006 A1   Nov. 11, 2010

(30) Foreign Application Priority Data

Dec. 12, 2007 (EP) .................................... 07122994

(51) Int. Cl.
*G01N 15/00* (2006.01)
(52) U.S. Cl.
USPC .......................................................... 73/865.5
(58) Field of Classification Search
USPC .............................................. 73/28.02, 865.5
See application file for complete search history.

(56) References Cited

U.S. PATENT DOCUMENTS 3,138,029 A * 6/1964 Rich ............................ 73/865.5
4,706,509 A   11/1987 Riebel (Continued)

FOREIGN PATENT DOCUMENTS

EP   1156320 A1   11/2001
EP   1681550 A1    7/2006

(Continued)

OTHER PUBLICATIONS

Adachi et al: "Unipolar and Bipolar Diffusion Charging of Ultrafine Aerosol Particles"; Journal of Aerosol Science, Vol. 16, Issue 2, 1985, pp. 109-123.

(Continued)

*Primary Examiner* — Peter Macchiarolo
*Assistant Examiner* — Alex Devito
(74) *Attorney, Agent, or Firm* — Larry Liberchuk

(57) ABSTRACT

The invention relates to a device that can reliably characterize a size distribution of electrically-charged airborne particles in an air flow under both stationary conditions and transient conditions. The device comprises a particle charging unit, a first particle precipitation unit located downstream of the particle charging unit, a second particle precipitation unit located downstream of the first particle precipitation unit, and a data evaluation unit. The first particle precipitation unit is arranged to partially reduce the concentration of electrically-charged airborne particles having a size larger than a first particle size limit, and to generate a first output signal corresponding to the precipitation of electrically-charged airborne particles inside the first particle precipitation unit. The second particle precipitation unit is arranged to precipitate substantially all entering electrically-charged airborne particles, and to generate a second output signal corresponding to the precipitation of electrically-charged airborne particles inside the second particle precipitation unit. The data evaluation unit is arranged to calculate, based on the output signals of the particle precipitation units, a particle number concentration and an average diameter of airborne particles larger than the lower particle size limit. The device enables the simultaneous generation and recording of output signals, and consequently an immediate determination of the particle number concentration and the average particle diameter at any instant.

7 Claims, 3 Drawing Sheets

(56) References Cited

U.S. PATENT DOCUMENTS

| | | | |
|---|---|---|---|
| 5,098,657 A | 3/1992 | Blackford et al. | |
| 5,572,322 A | 11/1996 | Noda | |
| 6,496,258 B1 | 12/2002 | Leipertz et al. | |
| 7,549,318 B2 * | 6/2009 | Burtscher et al. | 73/865.5 |
| 7,836,751 B2 * | 11/2010 | Marra | 73/28.02 |
| 2004/0184025 A1 | 9/2004 | Ohzu et al. | |
| 2006/0150754 A1 | 7/2006 | Burtscher et al. | |

FOREIGN PATENT DOCUMENTS

| | | | |
|---|---|---|---|
| GB | 2371362 A | * | 7/2002 |
| WO | 03021235 A1 | | 3/2003 |
| WO | 2005005965 A1 | | 1/2005 |
| WO | 2006016345 A1 | | 2/2006 |
| WO | 2006091095 A2 | | 8/2006 |
| WO | 2007000710 A2 | | 1/2007 |

OTHER PUBLICATIONS

Hinds, W.: "Aerosol Technology. Properties, Behaviour, Andmeasurement of Airborne Particles"; 2nd Edition (1999), John Wiley & Sons, Chapter 3, "Uniform Particle Motion"; pp. 43-74.

* cited by examiner

DEVICE FOR CHARACTERIZING A SIZE DISTRIBUTION OF ELECTRICALLY-CHARGED AIRBORNE PARTICLES IN AN AIR FLOW

FIELD OF THE INVENTION

The invention relates to a device for characterizing a size distribution of electrically-charged airborne particles in an air flow.

BACKGROUND OF THE INVENTION

To safeguard human health it is important to prevent health-hazardous airborne particles from being inhaled. Particularly health-hazardous airborne particles are ultra fine particles, which are particles that have an equivalent diameter between about 10 nm and about 2.5 µm, more in particular between about 20 nm and about 300 nm. Ultra fine particles can be formed as a result of an incomplete combustion process, and they can be emitted into air from the exhaust of combustion sources such as automobile traffic and other local combustion sources. It is well-known that inhalation of ultra fine particles can result in severe lung injuries.

Local detection of airborne particles preferably involves determination of the total particle number concentration and the average diameter of airborne particles.

A device for determining the aforementioned parameters is known from WO 2007/000710 A2. The known device is arranged to sample an air flow and comprises a particle concentration variation section, capable of causing a variation of the concentration of ultra fine particles between at least a first concentration level and a second concentration level during at least one time interval. The particle concentration variation section is located upstream from a particle sensing section, capable of producing a measurement signal varying in dependence of the variation between the first concentration level and the second concentration level. In response to the applied particle concentration variation, the known device determines measurement signals associated with varied particle concentration levels in a serial way during successive time intervals. A set comprising at least two measurement signals corresponding with a set of at least two varied particle concentration levels is required for determining the total particle number concentration and the average particle diameter. Different sets of measurement signals can be determined periodically to follow the evolution of the total particle number concentration and the average particle diameter in the course of time.

For an accurate determination of the total particle number concentration and the average diameter of airborne particles, the known device requires an environment wherein the total concentration of airborne particles and the particle size distribution (i.e. the particle concentration as a function of particle size) should be no more than only a slowly-varying function of time, preferably substantially stationary in time. During the time interval required to measure a set of serial measurement signals required for a single determination of the total particle number concentration and the average particle diameter, the total particle number concentration and the average particle diameter should remain substantially constant. This time interval cannot be made arbitrarily small because of minimum required demands on the measurement accuracy that normally necessitate signal averaging during at least a minimum period of time. For accurate operation in a non-stationary environment (such as existing at or near a location where motorized traffic is present), a device is required that can determine the total particle number concentration and the average diameter of airborne particles also under highly transient conditions wherein these parameters may rapidly change during the course of time. Such circumstances can for instance arise at or near a location where motorized traffic is present.

SUMMARY OF THE INVENTION

It is an object of the invention to provide a device of the kind set forth in the opening paragraph that can reliably characterize a size distribution of electrically-charged airborne particles in an air flow both under stationary conditions and under transient conditions.

According to the invention this object is realised in that the device comprises (a) a particle charging unit arranged to create the size distribution of electrically-charged airborne particles by electrically-charging airborne particles entering the device, (b) a first particle precipitation unit located downstream from the particle charging unit, arranged to partially reduce the concentration of electrically-charged airborne particles having a size larger than a first particle size limit, and to generate a first output signal corresponding to the precipitation of electrically-charged airborne particles inside the first particle precipitation unit, (c) a second particle precipitation unit located downstream from the first particle precipitation unit, arranged to precipitate substantially all entering electrically-charged airborne particles, and to generate a second output signal corresponding to the precipitation of electrically-charged airborne particles inside the second particle precipitation unit, and (d) a data evaluation unit arranged to calculate, based on the first output signal and the second output signal, a particle number concentration and an average diameter of airborne particles having a size larger than the first particle size limit.

The invention is based on the realisation that the inaccuracy of the known device under transient conditions is primarily the result of the fact that the determination of the total particle number concentration and the average diameter of electrically-charged airborne particles involves an adjustment of the particle size distribution in response to the consecutive (serial) application of two different electric field strengths in the particle concentration variation section, which requires a first finite amount of time. In addition, each successively-generated output signal (corresponding to a particle size distribution that is obtained through the application of an electric field strength) must be sampled for a second finite amount of time to allow for sufficient data averaging as required for obtaining a minimum specified degree of measurement accuracy. In case the particle concentration and/or the particle size distribution noticeably change during the first and/or second finite amount of time, inaccurate if not completely erroneous values for the total particle number concentration and the average particle diameter will be obtained.

The device according to the invention enables a more reliable characterization of a size distribution of electrically-charged airborne particles in an air flow by using, instead of successively-generated output signals, simultaneously-generated output signals from a first and a second particle precipitation unit, respectively. Each particle precipitation unit provides an output signal that is proportional to the length concentration of electrically-charged airborne particles that have precipitated in the particle precipitation unit. As the second particle precipitation unit is located downstream from the first particle precipitation unit, and as the latter is arranged to partially reduce the concentration of electrically-charged airborne particles having a size larger than a first particle size limit (meaning that for these particles the concentration is reduced to a non-zero value upon passing the first particle precipitation unit), the first and second output signals are indicative of different subsets of the size distribution of electrically-charged airborne particles that is to be characterized.

Combining the first and second output signal allows information to be obtained about the electrically-charged airborne particles that are larger than the first particle size limit. Both output signals are recorded simultaneously and can therefore also be averaged simultaneously, and are used as input for a data evaluation unit that is arranged to calculate the total particle number concentration and the average diameter of electrically-charged airborne particles larger than the first particle size limit from these output signals.

This calculation is based on the fact that the total particle number concentration for particles larger than the first particle size limit is found to be related to the first output signal corresponding to the controlled partial precipitation, inside the first particle precipitation unit, of electrically-charged airborne particles larger than the first particle size limit. The sum of the output signals generated by the particle precipitation units is found to be related to the total length concentration of the electrically-charged airborne particles in the air flow. The average diameter of the airborne particles larger than the first particle size limit is subsequently found by taking the ratio between the total length concentration and the total number concentration of airborne particles larger than the first particle size limit.

An embodiment of the device according to the invention is defined in claim 2. In this embodiment, the device further comprises a third particle precipitation unit located downstream from the first particle precipitation unit and upstream from the second particle precipitation unit, the third particle precipitation unit being arranged to precipitate substantially all entering electrically-charged airborne particles having a particle size smaller than a second particle size limit, and to generate a third output signal corresponding to the precipitation of electrically-charged airborne particles inside the third particle precipitation unit, wherein the data evaluation unit is further arranged to calculate, based on the first output signal, the second output signal, and the third output signal, a particle number concentration and an average diameter of airborne particles having a size larger than the second particle size limit.

The first, second, and third output signals (individually and in combination) were found to comprise information about the length concentration of all electrically-charged airborne particles, and the length concentration of electrically-charged airborne particles that have precipitated in and/or been transmitted by the first and the second particle precipitation unit, respectively.

This embodiment enables a more detailed characterization in multiple particle size intervals of the particle size distribution. Because all output signals are measured simultaneously, also their averaging over a finite period of time to improve the signal accuracy can be done simultaneously, which allows reliable information about the concentration and size distribution of airborne particles to be obtained also under transient conditions.

An embodiment of the device according to the invention is defined in claim 3. In this embodiment, the second particle size limit is such that at least 90% of the electrically-charged airborne particles larger than the first particle size limit in the air flow has a size smaller than the second particle size limit, and the data evaluation unit is further arranged to determine a relative width of the size distribution of electrically-charged airborne particles larger than the first particle size limit in the air flow from the average diameter of airborne particles having a size larger than the first particle size limit, and from the numerical value of the second particle size limit. This embodiment enables a more detailed characterization of the particle size distribution.

An embodiment of the device according to the invention is defined in claim 4. In this embodiment the particle charging unit is a diffusion charging unit comprising a corona discharge source, a porous screen electrode at least partially surrounding the corona discharge source, a reference electrode at least partially surrounding the porous screen electrode, and means for applying an electric potential difference between the porous screen electrode and the reference electrode. This embodiment enables a convenient and controllable way of electrically-charging a size distribution of airborne particles prior to their characterization by the device without being troubled by a substantial reduction in the particle concentration during the particle charging process due to electrostatic precipitation inside the particle charging unit, because particle diffusion charging is carried out at only a relatively low electric field strength.

An embodiment of the device according to the invention is defined in claim 5. In this embodiment the second particle precipitation unit comprises a particle filter disposed within a Faraday cage, the Faraday cage being connected via a sensitive current meter to a reference potential, the sensitive current meter being arranged to relay an output signal to the data evaluation unit. This embodiment enables a convenient way of characterizing an electrically-charged size distribution of airborne particles because the particle filter can readily be made to capture all airborne particles together with their electrical charge from an air flow.

An embodiment of the device according to the invention is defined in claim 6. In this embodiment the second particle precipitation unit comprises a parallel-plate precipitator, one of the plates of the parallel-plate precipitator being connected via a sensitive current meter to a reference potential, the sensitive current meter being arranged to relay an output signal to the data evaluation unit. This embodiment enables a convenient way of characterizing an electrically-charged size distribution of airborne particles because the electrical field strength between the plates of the parallel-plate precipitator can be readily adjusted to precipitate substantially all electrically-charged airborne particles together with their electrical charge from an air flow An embodiment of the device according to the invention is defined in claim 7. In this embodiment, the first particle size limit is set at a particle diameter within the size range between 10 nm and 20 nm. This particle size limit sets a lower effective particle size limit above which the airborne particle size distribution can be characterized on the basis of electrical charge associated with the particles, and is sufficiently low to enable characterization of a broad size range of airborne particles that incorporates most particle sizes of practical interest.

BRIEF DESCRIPTION OF THE DRAWINGS

Examples of the invention will now be described in detail with reference to the accompanying drawings, in which.

Figure 1A:
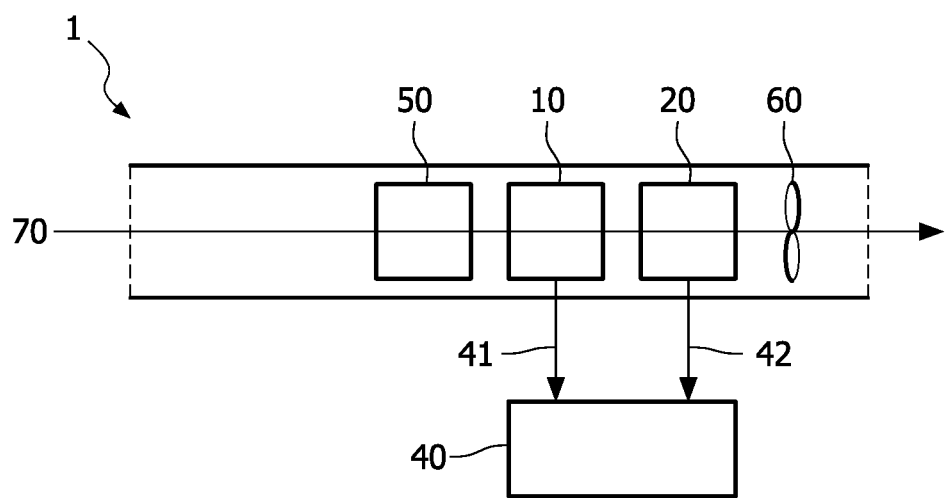
FIG. 1A is a schematic representation of a first embodiment of the device according to the invention.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION OF THE EMBODIMENTS

FIG. 1A shows a first embodiment of a device according to the invention. The device 1 is arranged to sample an air flow 70 comprising airborne particles by successively passing the air flow 70 through a first particle precipitation unit 10, and a second particle precipitation unit 20. For this purpose, the device 1 comprises a ventilator 60. Instead of a ventilator, another air displacement device may also be used, such as a pump or a heating element that is arranged to displace air by means of a thermal chimney effect caused by local differences in air density.

Prior to their entrance into the first particle precipitation unit 10, the airborne particles sampled by the device 1 are electrically-charged. For this purpose, the device 1 comprises a particle charging unit 50 located upstream from the first particle precipitation unit 10. As shown in FIG. 1B, the particle charging unit 50 comprises a corona discharge source 51, a porous screen electrode 52 at least partially surrounding the corona discharge source 51, a reference electrode 53 at least partially surrounding the porous screen electrode 52, and means 54 for applying an electric potential difference between the porous screen electrode 52 and the reference electrode 53. Particle charging occurs during passage of the airborne particles in the sampled air flow 70 through a conduit located between the porous screen electrode 52 and the reference electrode 53. By keeping the electric field between the porous screen electrode 52 and the reference electrode 53 preferably below 500 V/cm, particle charging occurs at a relatively low electric field strength, which warrants a minimal charging-induced loss of airborne particles (for example through deposition on the reference electrode 53) to occur inside the particle charging unit 50. Particle charging under these conditions is commonly referred to as particle diffusion charging. Other types of particle charging units would also be possible, such as a particle charging unit comprising a UV light source or through ionising radiation.

The first particle precipitation unit 10 is arranged to generate a first output signal 41, and the second particle precipitation unit 20 is arranged to generate a second output signal 42. As the airborne particles are electrically-charged via diffusion charging, the output signals 41 and 42 have a magnitude that is proportional to the length concentration of the electrically-charged airborne particles that have precipitated in the particle precipitation units 10 and 20, respectively.

As shown in FIG. 1B, the first particle precipitation unit 10 comprises a parallel-plate precipitator 11. In a first mode of operation of the first particle precipitation unit 10, the parallel-plate precipitator 11 is arranged to produce a first electric field $E_1$ between its plates. The magnitude of the electric field $E_1$ is such that the concentration of electrically-charged airborne particles that pass between the plates of the parallel-plate precipitator 11, and that have a particle size larger than a first particle size limit $d_1$, is reduced to a non-zero value. This is illustrated in FIG. 3A, that schematically shows the fractional particle precipitation efficiency as a function of particle size for airborne particles that have been electrically-charged using diffusion charging. From FIG. 3A it is clear that when the first electric field $E_1$ is applied between the plates of the parallel-plate precipitator 11, all electrically-charged particles sized larger than the first particle size limit $d_1$ have a fractional particle precipitation efficiency smaller than unity so that their concentration is reduced to a non-zero value. It is also still possible to induce only a partial precipitation efficiency inside the parallel-plate precipitator 11 with respect to electrically-charged particle that are smaller than the first particle size limit $d_1$.

In the parallel-plate precipitator 11, precipitation of electrically-charged airborne particles occurs on the plate that is connected via a sensitive current meter (not shown) to a reference potential, the current meter being capable of generating the first output signal 41 that represents the amount of electrical charge that is deposited per unit time in the parallel-plate precipitator 11.

As shown in FIG. 1B, the second particle precipitation unit 20 comprises a particle filter 21 disposed within a Faraday cage 22. The particle filter 21 is capable of capturing airborne particles from the air flow 70 passing through the Faraday cage 22. The Faraday cages 22 is connected via a sensitive current meter (not shown) to a reference potential, the current meter being capable of generating the second output signal 42 that represent the amount of electrical charge that is deposited per unit time in the particle filters 21.

For the purpose of the invention, the second particle precipitation unit may alternatively be embodied as a parallel-plate precipitator that is arranged to produce an electric field between its plates that is capable of precipitating substantially all entering electrically-charged airborne particles inside the second particle precipitation unit. In the embodiments shown in FIG. 1B, the first particle precipitation unit 10 and the second particle precipitation unit 20 are ultra fine particle precipitation units, capable of precipitating particles with an equivalent diameter in a range of approximately 10 nm to 2.5 μm, preferably approximately 15 nm to 500 nm, most preferably approximately 20 nm to 300 nm. In ordinary ambient air, the largest contribution to the total particle number concentration normally comes from airborne particles smaller than 300 nm, which are usually produced by combustion sources such as automobile engines.

The first output signal 41 and the second output signal 42 are recorded by a data evaluation unit 40 that is arranged to calculate from these output signals a total particle number concentration and an average particle diameter relating to particles larger than the first particle size limit $d_1$. Recording the first output signal 41 and the second output signal 42 simultaneously allows for an immediate determination of the total particle number concentration and the average particle diameter also under transient conditions.

In the first mode of operation of the device 1, the first output signal 41 is an electrical current of magnitude $I_1$-$I_2$, while the second output signal 42 is an electrical current of magnitude $I_2$, wherein $I_1$ represents the electrical current associated with the capturing of substantially all electrically-charged airborne particles having a size larger than the first particle size limit $d_1$. In other words, the magnitude of the electrical current $I_1$ can be obtained by the sum of the first output signal 41 and the second output signal 42, while the magnitude of the electrical current $I_2$ is obtained directly from the second output signal 42.

Without wishing to be bound by any theory, hereinafter a more detailed explanation is provided of how the electrical currents $I_1$ and $I_2$ relate to the concentration and size distribution of airborne particles entering the device 1 and the various process and device parameters existing therein. Under conditions of particle diffusion charging, it was found that the average number of elementary electrical charges $p_{av}$ on a particle of effective diameter d obeys the relationship $$p_{av} = A \cdot d \qquad (1)$$

with A denoting a constant which is substantially independent of d.

The value for the constant A in Eq. (1) and also more detailed information about the particle charging characteristics as a function of the various process and charging parameters existing in the particle charging unit 60 may be obtained either empirically or with the help of, for example, the Fuchs theory for aerosol charging (see for instance M. Adachi et al., Journal of Aerosol Science, 16 (1985) pp. 109-123).

The electrical current $I_1$ was found to obey the relationship $$I_1 = \int_{d=0}^{\infty} p_{av} e\phi \frac{dN(d)}{d\ln(d)} d\ln(d) \qquad (2)$$
$$= Ae\phi \int_{d=0}^{\infty} d \frac{dN(d)}{d\ln(d)} d\ln(d)$$
$$= Ae\phi L$$

wherein the integration is carried out over all particle sizes d of all airborne particles. In Eq. (2), e denotes the elementary electrical charge, $\phi$ the volumetric air flow through the device 1, L is the particle length concentration, and N(d) denotes the particle number concentration as a function of particle size. It is implicitly assumed that all electrically-charged airborne particles that enter the device 1 are also trapped therein. The ratio $dN(d)/d\ln(d)$ represents the normalized particle size distribution. Thus, $I_1$ is proportional to the particle length concentration L. It is noted here that the integration of the normalized particle size distribution over the logarithm of the particle size yields the total particle number concentration N according to $$N = \int_{d=0}^{\infty} \frac{dN(d)}{d\ln(d)} \cdot d\ln(d) \qquad (3)$$

Concerning the first particle precipitation unit 10 in the device 1, the applied electric field $E_1$ between the plates of the parallel-plate precipitator 11 induces a fractional precipitation degree $\xi(E_1)$ of electrically-charged airborne particles of diameter d according to $$\xi(E_1) = \frac{p_{av} e C E_1 \lambda}{3\pi \eta d v_{air} \delta} \qquad (4)$$

with $p_{av}$ given by Eq. (1).

In Eq. (4), C denotes the particle-size-dependent Cunningham slip correction factor (for more detailed information, see, for example, W. C. Hinds, Aerosol Technology. Properties, Behaviour and Measurement of Airborne Particles, $2^{nd}$ Ed. (1999), John Wiley & Sons, Chapter 3), X denotes the length of the plates of the parallel-plate precipitator 11, $\delta$ denotes the spacing between the plates of the parallel-plate precipitator 11, $v_{air}$ is the average air flow speed between the plates of the parallel-plate precipitator 11, and $\eta$ is the air viscosity.

The electrical current $I_2$, being the second output signal 42, is derived from the electrically-charged particles that have escaped precipitation inside the parallel-plate precipitator 11 and is approximately given by $$I_2 = \int_{d=d_1}^{\infty} p_{av} e\phi [1 - \xi(E_1)] \frac{dN(d)}{d\ln(d)} d\ln(d) \qquad (5)$$

wherein the integration is carried out over all particle sizes $d > d_1$, $d_1$ denoting the first particle size limit $d_1$ at which $\xi(E_1) \approx 1$. It is noted here that Eq. (5) can be rewritten in a more elaborate form by not just involving the average electrical particle charge $p_{av}e$ on a particle of any given effective diameter d but instead the statistical particle charge distribution on particles of any given effective diameter d (the reader is referred to the earlier mentioned reference of M. Adachi et al. for more detailed information).

A suitable value for $d_1$ is the effective particle diameter at which $p_{av} \approx 1$. Dependent on the chosen particle charging conditions, $d_1$ is 10 nm, preferably 15 nm, more preferably 20 nm, thereby setting an upper limit to the magnitude of the first electric field $E_1$ to ensure that $\xi(E_1) < 1$ for $d > d_1$. The latter numerical value of $d_1$ is sufficiently low to justify the assumption that airborne particles sized smaller than $d_1$ will in many cases of practical interest not make a significant contribution to either the electrical current $I_1$ or the total number concentration N of all airborne particles in ordinary ambient air.

The difference between the electrical currents $I_1$ and $I_2$, being the first output signal 41, can now be described according to $$I_1 - I_2 \approx \int_{d=d_1}^{\infty} p_{av} e\phi \xi(E_1) \frac{dN(d)}{d\ln(d)} d\ln(d) = C_1(d_{av}, \sigma) N(d > d_1) \qquad (6)$$

with $N(d > d_1)$ denoting the number concentration of electrically-charged airborne particles larger than $d_1$. At a relatively small first particle size limit $d_1 \approx 10$-20 nm, $N(d > d_1)$ will in many cases be close to the number concentration N of all airborne particles. The parameter $C_1(d_{av}, \sigma)$ represents a constant whose value may be expected to depend to a certain extent on both the average particle size $d_{av}$ of all electrically-charged airborne particles larger than $d_1$ and the characteristics of the particle size distribution as accounted for by the parameter $\sigma$. For example, $\sigma$ may represent the geometric standard deviation in a log-normal particle size distribution. In case the majority of airborne particles is sized below about 150-200 nm diameter, which is normally the case in ambient air, the parameter $C_1(d_{av}, \sigma)$ was found to be substantially independent of both $d_{av}$ and $\sigma$, yielding the result that $$N(d > d_1) = \frac{(I_1 - I_2)}{C_1} \qquad (7)$$

with $C_1$ being a constant.

For the average particle diameter $d_{av}$ of the electrically-charged airborne particles larger than $d_1$ one obtains $$d_{av} = \frac{L}{N(d > d_1)} = \left(\frac{I_1}{I_1 - I_2}\right) \cdot \frac{C_1}{Ae\phi} \qquad (8)$$

The outcome for $d_{av}$ in Eq. (8) can be used to check the correctness of the assumption that the majority of airborne particles is sized less than about 150-200 nm. If not, the dependence of $C_1(d_{av},\sigma)$ on both $d_{av}$ and $\sigma$ must be accounted for. The particle size distribution can, for example, be approximately represented as a log-normal particle size distribution characterized with the parameters N, $d_{av}$ and $\sigma$ according to $$dN(d) = \frac{N}{\sqrt{2\pi}\ln\sigma}\exp\left\{\frac{\left[\ln(d) - \ln(d_{av}) + \frac{\ln^2\sigma}{2}\right]^2}{2\cdot[\ln(\sigma)]^2}\right\}d\ln(d) \qquad (9)$$

By combining Eqs. (1), (4) and (6)-(9), the relationships $C_1(d_{av},\sigma)$ can be established for known particle size distributions (and thus with known values for $d_{av}$, $\sigma$ and $N(d>d_1)$) and can be used to check the outcomes for $N(d>d_1)$ and $d_{av}$ according to Eqs. (7) and (8) for internal consistency, if necessary in an iterative manner. Alternatively, the relationships $C_1(d_{av}, \sigma)$ can be established empirically for known particle size distributions with known values for $N(d>d_1)$ and $d_{av}$.

Figure 3A:
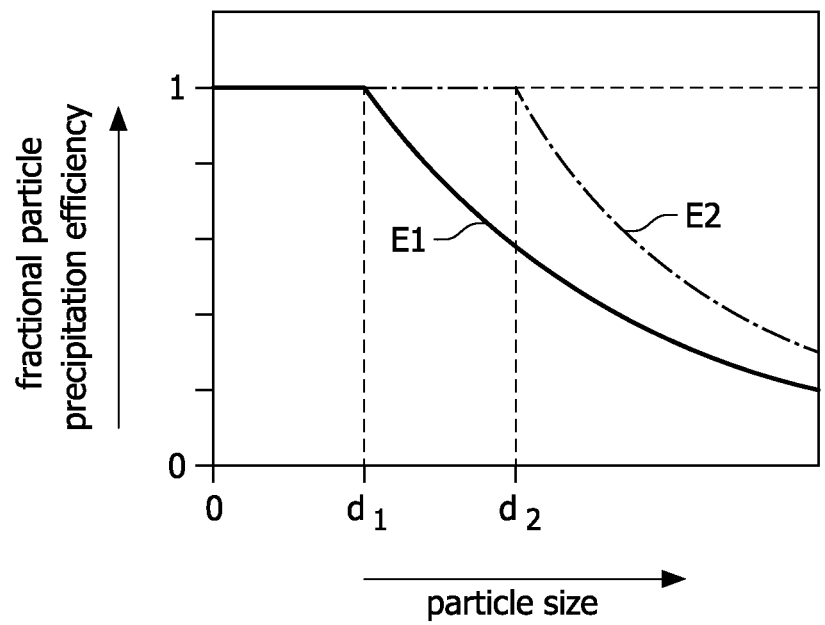
FIG. 3A is a graph that schematically shows the fractional particle precipitation efficiency of diffusion-charged particles as a function of particle size, for a particle precipitation unit comprising a parallel-plate precipitator having an electric field $E_1$ or an electric field $E_2$ applied between its plates.
Figure 3B:
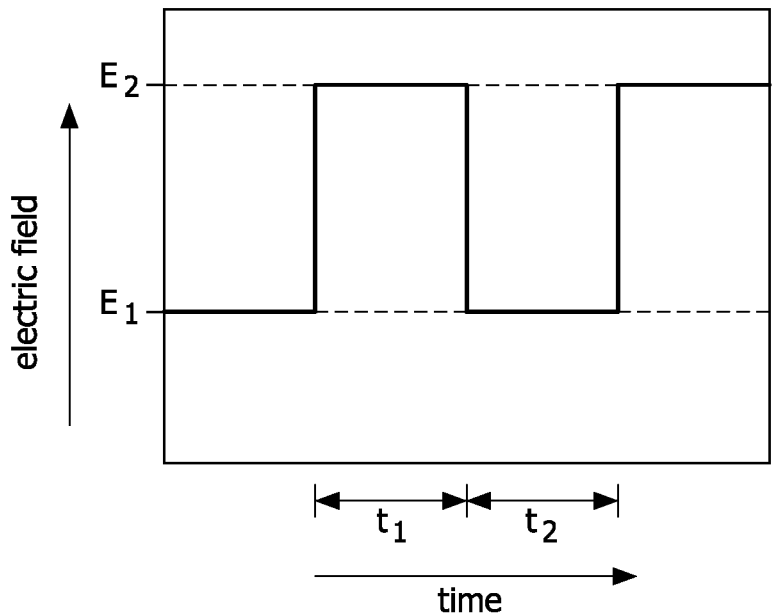
FIG. 3B is a graph that schematically shows the successive application of a first electric field $E_1$ and a second electric field $E_2$ between the plates of a parallel-plate precipitator comprised in a particle precipitation unit.

In a second mode of operation of the first particle precipitation unit 10, the first electric field $E_1$ and a second electric field $E_2$ are successively applied between the plates of the parallel-plate precipitator 11. This is illustrated in FIG. 3B that schematically shows the successive application of the first electric field $E_1$ and the second electric field $E_2$, during a first time period $t_1$ and a second time period $t_2$, respectively.

The magnitude of the second electric field $E_2$ is higher than that of the first electric field $E_1$, and such that the concentration of electrically-charged airborne particles with a size smaller than a second particle size limit $d_2$ is reduced to zero, while the concentration of electrically-charged airborne particles with a size larger than the second particle size limit $d_2$ is reduced to a non-zero value, the second particle size limit $d_2$ being higher than the first particle size limit $d_1$. This is illustrated in FIG. 3A, that schematically shows the fractional particle precipitation efficiency of electrically-charged particles as a function of particle size. From FIG. 3A it is clear that when the electric field $E_1$ is applied between the plates of the parallel-plate precipitator 11, all electrically-charged particles larger than the first particle size limit $d_1$ have a fractional particle precipitation efficiency smaller than unity so that their concentration is reduced to a non-zero value. When the electric field $E_2$ is applied between the plates of the parallel-plate precipitator 11, only the electrically-charged particles larger than the second particle size limit $d_2$ have a fractional particle precipitation efficiency smaller than unity, while the electrically-charged particles smaller than the second particle size limit $d_2$ have a fractional particle precipitation efficiency of unity so that in the air flow 70 exiting the first particle precipitation unit 10, their concentration is reduced to zero.

Depending on the electric field applied between the plates of the parallel-plate precipitator 11 ($E_1$ or $E_2$), the output signal 42 either carries information about electrically-charged airborne particles larger than the first particle size limit $d_1$ that have escaped precipitation in the parallel-plate precipitator 11, or about electrically-charged airborne particles larger than the second particle size limit $d_2$ that have escaped precipitation in the parallel-plate precipitator 11. The data evaluation unit 40 is arranged to calculate from the first output signal 41 and the second output signal 42 a particle number concentration and an average particle diameter, either relating to electrically-charged airborne particles larger than the first particle size limit $d_1$, or relating to electrically-charged airborne particles larger than the second particle size limit $d_2$. In this way, a more detailed characterization of the particle size distribution can be performed.

As the second mode of operation requires the successive application of two different electric fields between the plates of the parallel-plate precipitator 11, the concentration and size distribution of airborne particles needs to be substantially constant for a period of time equal to the sum of $t_1$ and $t_2$. By monitoring whether the sum of the first and second output signals 41 and 42 remains substantially constant during the time interval $t_1+t_2$, it can be decided whether the device 1 can only be operated in the first mode (also useable under transient conditions), or whether the circumstances are sufficiently stationary to also permit the device 1 to be operated in the second mode in order to perform a more detailed characterization of the size and concentration distribution of the airborne particles.

Without wishing to be bound by any theory, hereinafter a more detailed explanation is provided of how, in the second mode of operation of the device 1, the concentration of electrically-charged airborne particles $N(d>d_2)$ larger than the second particle size $d_2$ can be determined from the first and second output signals 41 and 42, respectively.

In the second mode of operation of the device 1, the first output signal 41 is an electrical current of magnitude $I_1$-$I_3$ while the second output signal 42 is an electrical current of magnitude $I_3$, which is given by $$I_3 = \int_{d=d_2}^{\infty} p_{av}e\varphi[1-\xi(E_2)] \cdot \frac{dN(d)}{d\ln(d)} \cdot d\ln(d) \qquad (10)$$

The difference between $I_1$ and $I_3$ yields information about the electrically-charged airborne particles larger than the second particle size limit $d_2$ according to $$\begin{aligned}I_1 - I_3 &\approx \int_{d=d_1}^{d_2} p_{av}e\phi\frac{dN(d)}{d\ln(d)}d\ln(d) + \\ &\quad \int_{d=d_2}^{\infty} p_{av}e\phi\xi(E_2)\frac{dN(d)}{d\ln(d)}d\ln(d) \\ &\approx Ae\phi\frac{d_2+d_1}{2}[N(d>d_1) - N(d>d_2)] + \\ &\quad C_2(d_{av},\sigma)N(d>d_2)\end{aligned} \qquad (11)$$

The first term on the right hand side of Eq. (11) is proportional to the particle length concentration of electrically-charged airborne particles sized larger than $d_1$ but smaller than $d_2$. The second term on the right hand side of Eq. (11) contains the parameter $C_2(d_{av}, \sigma)$ which can be obtained or inferred a priori for any particle size distribution characterized with the parameters N, $d_{av}$ and the effective particle size distribution parameter $\sigma$ by calculating or measuring the electrical currents $I_1$ and $I_3$ as a function of the various process, charging, and design parameters in the device 1 and the parameters N, $d_{av}$ and $\sigma$. $N(d>d_2)$ denotes the number concentration of airborne particles larger than the second particle size limit $d_2$. The particle size limits $d_1$ and $d_2$ can be obtained at electric fields of magnitude $E_1$ and $E_2$, respectively, in the parallel-plate precipitator 11 as the roots $d_1$ and $d_2$ at which $$\frac{p_{av}eCE\lambda}{3\pi\eta dv_{air}\delta} - 1 = 0 \quad (12)$$

(see Eq. (4)).

With known values for $d_1$ and $d_2$, also $N(d>d_1)$ and $N(d>d_2)$ can be inferred for any known particle size distribution, which allows the parameter $C_2(d_{av}, \sigma)$ to be inferred when the electrical currents $I_1$, $I_2$, and $I_3$ are known. When the electrical currents $I_1$, $I_2$, and $I_3$ are subsequently measured with respect to an unknown aerosol with an unknown particle size distribution, a recording of the electrical currents $I_1$ and $I_2$ suffices to obtain $N(d>d_1)$ and $d_{av}$ according to Eqs. (7) and (8). The electrical currents $I_1$ and $I_3$ can then subsequently be used to also infer the concentration $N(d>d_2)$ according to Eq. (11) with the help of the known parameter $C_2(d_{av}, \sigma)$, most easily so in case $C_2(d_{av},\sigma)$ is only weakly dependent on a. In case a more accurate determination of $N(d>d_2)$ is desired, the effective particle size distribution parameter 6 must be known a priori in order to be able to determine upfront a more accurate value for $C_2(d_{av}, \sigma)$ at a known value for $d_{av}$. This can also be useful for determining a more accurate value for the parameter $C_1(d_{av}, \sigma)$ introduced in Eq. (6). Specifically for a log-normal particle size distribution, $\sigma$ represents the standard deviation of the particle size distribution, and was found to be approximately related to $d_{av}$ according to $$\sigma = \exp\left\{2 - 2\sqrt{\left[1 - \ln\sqrt{\left(\frac{d_{upper}}{d_{av}}\right)}\right]}\right\} \quad (13)$$

with the particle size $d_{upper}$ obtained as the root $d=d_{upper}$ from Eq. (12) for an electric field strength $E_{upper}$ applied between the plates of the parallel-plate precipitator 11 at which the electrical current $I_2$ measured by the second particle precipitation unit 20 is reduced down to only a few percent of the sum of the electrical currents $I_1$-$I_2$ and $I_2$ measured by the first particle precipitation unit 10 and the second particle precipitation unit 20. Clearly, $d_{upper}$ represents an effective upper particle size of the entire particle size distribution with more than 90% of the electrically-charged airborne particles larger than the first particle size limit $d_1$ being sized smaller than $d_{upper}$. The ratio between $d_{av}$ and $d_{upper}$ can be conveniently used to evaluate the relative width of the particle size distribution as expressed by the parameter 6.

The determination of $N(d>d_2)$ in addition to $N(d>d_1)$ enables a more detailed characterization of the particle size distribution. The average particle diameter $d_{av}(d>d_2)$ for airborne particles larger than the second particle size limit $d_2$ can be inferred from $N(d>d_1)$, $N(d>d_2)$, and $d_{av}$ according to $$d_{av}(d>d_2) = \frac{N(d>d_1)d_{av} - [N(d>d_1) - N(d>d_2)] \cdot \frac{d_1 + d_2}{2}}{N(d>d_2)} \quad (14)$$

It will be clear from the above that a series of successively increasing field strengths ($E_1$, $E_2$, $E_3$, etc.) can be serially applied between the plates of the parallel-plate precipitator 11, thereby allowing a series of successively reducing particle number concentrations ($N(d>d_1)$, $N(d>d_2)$, $N(d>d_3)$, etc.) to be serially determined, thereby yielding even more information about the particle size distribution characteristics. The degree of constancy of the sum of the first and second output signals 41 and 42, being the electrical current $I_1$, can be used to estimate the reliability and/or relative accuracy of the successively obtained particle number concentrations. The highest reliability is obtained when the sum of the first and second output signals 41 and 42 remains substantially constant during the total time interval required to determine the particle number concentration series.

Figure 2A:
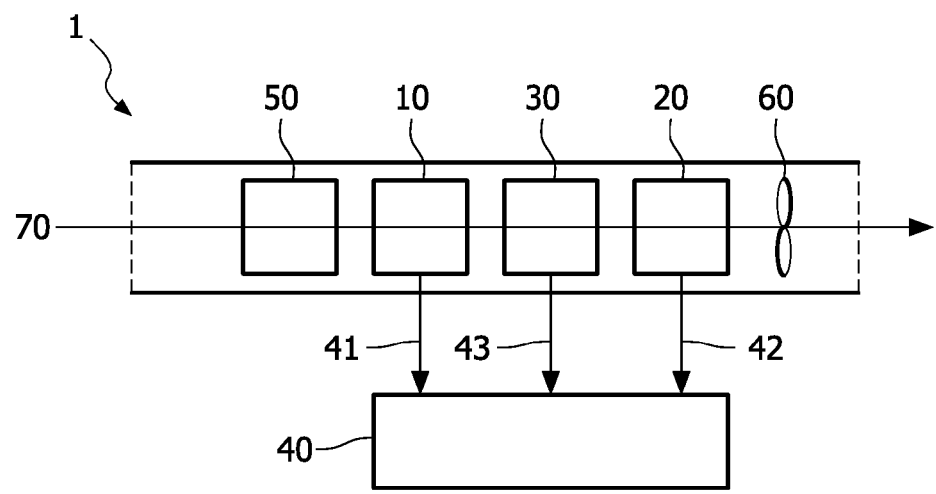
FIG. 2A is a schematic representation of a second embodiment of the device according to the invention.

FIG. 2A shows a second embodiment of a device according to the invention. In addition to the first particle precipitation unit 10 and the second particle precipitation unit 20, the device 2 further comprises a third particle precipitation unit 30, located downstream from the first particle precipitation unit 10 and upstream from the second particle precipitation unit 20.

Figure 2B:
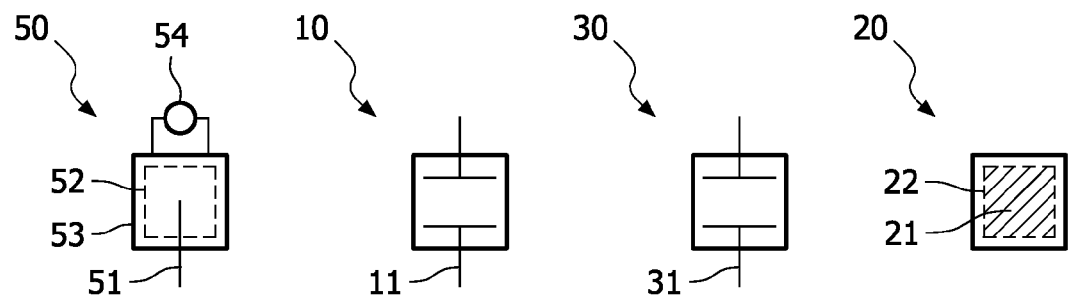
FIG. 2B is a schematic representation of embodiments of a particle charging unit, a first particle precipitation unit, a second particle precipitation unit, and a first particle precipitation unit, respectively, for use in the embodiment of FIG. 2A.

As shown in FIG. 2B, the third particle precipitation unit 30 comprises a parallel-plate precipitator 31, in which precipitation of electrically-charged airborne particles occurs on the plate that is connected via a sensitive current meter (not shown) to a reference potential, the current meter being capable of generating a third output signal 43 that represents the amount of electrical charge that is deposited per unit time in the parallel-plate precipitator 31.

The parallel-plate precipitator 31 is arranged to produce a second electric field $E_2^*$ between its plates. The magnitude of the second electric field $E_2^*$ is such that the concentration of electrically-charged airborne particles with a size smaller than the second particle size limit $d_2$ is reduced to zero in the airflow exiting the parallel-plate precipitator 31, while the concentration of electrically-charged airborne particles with a size larger than the second particle size limit $d_2$ is reduced to a non-zero value, the second particle size limit $d_2$ being higher than the first particle size limit $d_1$. Specifically, the magnitude of the electric field $E_2^*$ in the third particle precipitation unit 30 can be increased to such an extent that at least 90% of the electrically-charged airborne particles precipitates inside the serially-combined first particle precipitation unit 10, wherein an electric field $E_1$ is applied between the plates of the parallel-plate precipitator 11, and third particle precipitation unit 30, wherein an electric field $E_2^*$ is applied between the plates of the parallel-plate precipitator 31. In that case, the second particle size limit $d_2$ represents the particle size $d_{upper}$ introduced in Eq. (13). According to Eq. (13), the ratio $d_{av}/d_{upper}$ can be used to evaluate the effective width of the particle size distribution in terms of an effective size deviation parameter $\sigma$.

In the device 2, the simultaneously-generated first, second, and third output signals 41, 42 and 43, respectively, represent separate electrical currents which, when taken together, add up to the total current $I_1$ according to Eq. (2), representing the total charge of all electrically-charged airborne particles that is precipitated per unit time in any of the particle precipitation units 10, 30, 20 of the device 2.

Specifically, the output signal 41 represents the electrical current $I_1$-$I_2$ according to Eq. (6). The sum of the output signals 42 and 43 represents the electrical current $I_2$ according to Eq. (5).

Figure 1B:
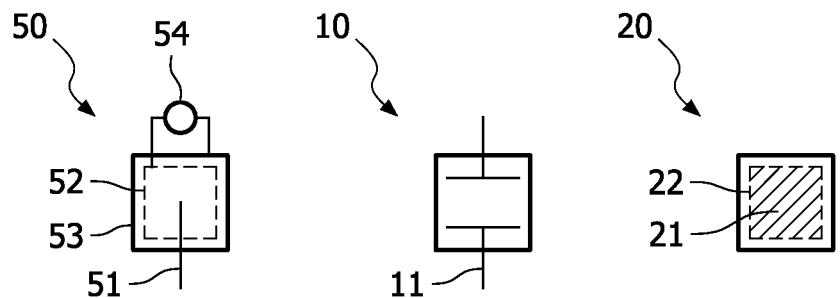
FIG. 1B is a schematic representation of embodiments of a particle charging unit, a first particle precipitation unit, and a second particle precipitation unit, respectively, for use in the embodiment of FIG. 1A.

The output signal 42 represents the current $I_3$ according to Eq. (10) (which accounts for an electric field strength $E_2$) when the electric field strength $E_2^*$ in the parallel-plate precipitator 31 is chosen such that $$1-\xi(E_2)=(1-\xi(E_1))(1-\xi(E^*_2)) \quad (15)$$

with $\xi(E)$ given by Eq. (4). It should be noted that the electric fields $E_2$ (applied between the plates of the parallel-plate precipitator 11 in FIG. 1B to accomplish a substantially complete precipitation of all entering electrically charged airborne particles having a particle size smaller than $d_2$) and $E_2^*$ (applied between the plates of the parallel-plate precipitator 31 in FIG. 2B to accomplish a substantially complete precipitation of all electrically charged airborne particles having a particle size smaller than $d_2$ that enter the serially-combined parallel-plate precipitators 11 and 31) differ from each other because of the influence of the electric field strength $E_1$ applied between the plates of the parallel-plate precipitator 11 in FIG. 2B on the overall precipitation of electrically-charged particles in the serially-combined parallel-plate precipitators 11 and 31. It is implicitly assumed here that the process and design parameters pertaining to the parallel-plate precipitator 11 in FIG. 1B and the parallel-plate precipitators 11 and 31 in FIG. 2B are the same. If not, this could be readily accounted for by anyone skilled in the art.

The output signal 43 in FIG. 2A represents the current $I_2$-$I_3$ with $I_2$ and $I_3$ given by Eqs. (5) and (10), respectively, while accounting for Eq. (15).

The output signals 41, 42, and 43 from the device 2 can be used to characterize the size distribution of electrically-charged airborne particles, and obtain values for $d_{av}$, $\sigma$, $N(d>d_1)$ and $N(d>d_2)$ in an analogous way as explained above for the device 1 when operated in the second mode of operation.

Instead of limiting the number of particle precipitation units in the device 2 to three (as shown in FIG. 2A), the device 2 can comprise a plurality of particle precipitation units, each capable of inducing a different degree of electrically-charged particle precipitation for particles sized larger than a particle size limit by imposing different electric field strengths between the plates of the parallel-plate precipitators, thereby enabling the simultaneous determination of a series of particle number concentrations for particle sizes larger than a corresponding series of particle size limits. The determined series of particle number concentrations can additionally be used to determine the particle size distribution, and to infer from this determined particle size distribution an effective particle size distribution parameter $\sigma$ (for example with the help of Eq. (9)) and to check from there the correctness of the a priori assumed value for a for the particle size distribution and/or the correctness of the predetermined value of a established according to Eq. (13). It is even possible in this way to determine the value for a in an iterative manner until a series of particle number concentrations for a corresponding series of particle size intervals is determined that is consistent with that value for $\sigma$, thus involving an internal consistency check.

Instead of involving only one single value $\sigma$ to account for the effective width of the particle size distribution, it should be clear that it may sometimes be necessary to involve several different size distribution parameters $\sigma_i$ to more accurately account for the characteristics of the particle size distribution, for example when this particle size distribution is the result of a superposition of several log-normal particle size distributions, each log-normal size distribution i being described by its own set of parameters $N_i$, $d_{av,i}$, and $\sigma_i$ according to Eq. (8).

An advantage of the embodiment shown in FIG. 2A is that even under circumstances wherein the concentration and size distribution of airborne particles is not substantially constant in time, a reliable and accurate characterization of the particle size distribution can be performed, also under highly transient conditions.

While the invention has been illustrated and described in detail in the drawings and foregoing description, such illustration and description are to be considered illustrative or exemplary and not restrictive; the invention is not limited to the disclosed embodiments. Variations to the disclosed embodiments can be understood and effected by those skilled in the art in practicing the claimed invention, from a study of the drawings, the disclosure, and the appended claims. In the claims, the word "comprising" does not exclude other elements, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A device for characterizing a size distribution of electrically-charged airborne particles in an air flow, comprising:
   a particle charging unit arranged to create the size distribution of electrically-charged airborne particles by electrically-charging airborne particles entering the device,
   a first particle precipitation unit located downstream from the particle charging unit, arranged to, for each size larger than a first particle size limit, partially reduce the concentration of electrically-charged airborne particles having said each size, and to generate a first output signal corresponding to the precipitation of electrically-charged airborne particles inside the first particle precipitation unit,
   a second particle precipitation unit located downstream from the first particle precipitation unit, arranged to precipitate substantially all entering electrically-charged airborne particles, and to generate a second output signal corresponding to the precipitation of electrically-charged airborne particles inside the second particle precipitation unit,
   a data evaluation unit arranged to calculate, based on the first output signal and the second output signal, a particle number concentration and an average diameter of airborne particles having a size larger than the first particle size limit.

2. The device according to claim 1, further comprising a third particle precipitation unit located downstream from the first particle precipitation unit and upstream from the second particle precipitation unit, the third particle precipitation unit being arranged to precipitate substantially all entering electrically-charged airborne particles having a particle size smaller than a second particle size limit, and to generate a third output signal corresponding to the precipitation of electrically-charged airborne particles inside the third particle precipitation unit, wherein the data evaluation unit is further arranged to calculate, based on the first output signal, the second output signal, and the third output signal, a particle number concentration and an average diameter of airborne particles having a size larger than the second particle size limit.

3. The device according to claim 2, wherein the second particle size limit is such that at least 90% of the electrically-charged airborne particles larger than the first particle size limit in the air flow has a size smaller than the second particle size limit, and wherein the data evaluation unit is further arranged to determine a relative width of the size distribution of electrically-charged airborne particles larger than the first particle size limit in the air flow from the average diameter of airborne particles having a size larger than the first particle size limit, and from the numerical value of the second particle size limit.

4. The device according to claim 1, wherein the particle charging unit is a diffusion charging unit comprising a corona discharge source, a porous screen electrode at least partially surrounding the corona discharge source, a reference electrode at least partially surrounding the porous screen electrode, and means for applying an electric potential difference between the porous screen electrode and the reference electrode.

5. The device according to claim 1, wherein the second particle precipitation unit comprises a particle filter disposed within a Faraday cage, the Faraday cage being connected via a sensitive current meter to a reference potential, the sensitive current meter being arranged to relay the second output signal to the data evaluation unit.

6. The device according to claim 1, wherein the second particle precipitation unit comprises a parallel-plate precipitator, one of the plates of the parallel-plate precipitator being connected via a sensitive current meter to a reference potential, the sensitive current meter being arranged to relay the second output signal to the data evaluation unit.

7. The device according to claim 1, wherein the first particle size limit is set at a particle diameter within the size range between 10 nm and 20 nm.

\* \* \* \* \*